United States Patent [19]

Terry

[11] 4,157,859
[45] Jun. 12, 1979

[54] SURGICAL MICROSCOPE SYSTEM

[76] Inventor: Clifford Terry, 7087 Columbus, Anaheim, Calif. 92807

[21] Appl. No.: 800,613

[22] Filed: May 26, 1977

[51] Int. Cl.² .............................................. G02B 21/20
[52] U.S. Cl. ................................. 350/35; 128/303 R; 350/36; 350/40; 350/145; 351/13; 351/39
[58] Field of Search ................ 351/13, 39, 40; 350/35, 350/36, 40, 145; 128/303 R, 395

[56] References Cited

U.S. PATENT DOCUMENTS

| 1,523,528 | 1/1925 | Henker | 351/13 X |
|---|---|---|---|
| 3,183,519 | 5/1965 | Harris et al. | 351/13 X |
| 3,542,458 | 3/1968 | Volk | 351/13 X |
| 3,969,019 | 7/1976 | Nohda | 351/13 |
| 4,046,463 | 9/1977 | LaRussa | 351/13 |

Primary Examiner—Paul A. Sacher
Attorney, Agent, or Firm—John G. Mesaros

[57] ABSTRACT

A surgical microscope apparatus and method for using the same for use while suturing an incision in the cornea for reconfiguring the cornea to a spherical surface having a radius of curvature of a predetermined magnitude, the microscope system including means for projecting an image onto the cornea, means for optically splitting the image into a plurality of images within the surgical field of view for viewing through the binocular eyepieces and means for adjusting the optical system to orient the images into a predetermined alignment and configuration indicative of the radius of curvature, the alignment and configuration occurring when the cornea sutures are tensioned correctly to indicate a spherical surface of the predetermined radius of curvature. The means for optically splitting the images are so-positioned to permit a portion of the surgical field of view to pass through the microscope undeviated to enable the surgeon to utilize the necessary suturing tools without multiple images of the tools. In a first embodiment a fixed location prism array is utilized for optically splitting the image and the optical system is adjusted by varying the magnification powers of the microscope. In a second embodiment, rotary prisms are in a fixed position within the optical path for optically splitting the image and the optical system is adjusted by varying the prism power. The optical system adjusting means in either embodiment are calibrated to an electrical signal indicative of the radius of curvature.

31 Claims, 18 Drawing Figures

FIG_12A

FIG_12B

FIG_12C

SURGICAL MICROSCOPE SYSTEM

BACKGROUND OF THE INVENTION

The background of the invention will be discussed in two parts.

1. Field of the Invention

This invention relates to microscopes and more particularly to a microscope for performing surgery on the eye.

2. Description of the Prior Art

With ophthalmic surgery, for example, surgery involving cataracts, ideally it is desirable to reconfigure the cornea after the operation to the same radius of curvature existing prior to the operation. In the human eye, the radius of curvature varies from individual to individual with a normal range being between 40 and 50 diopters which correspond to radii of curvature of 8.44 millimeters to 6.75 millimeters, respectively. In order to ascertain the radius of curvature prior to the operation, measurements are taken along certain angles or meridians. Heretofore, such measurements have been taken by means of telescopic instruments known as ophthalmometers or Keratometers. A corneal measurement technique is shown and described in U.S. Pat. No. 3,895,860 and a Keratometer device is referred to in U.S. Pat. No. 3,972,602.

In measuring the size or radius of curvature of the cornea, the instrument heretofore used is the Keratometer or opthalmometer. Such a device is a monocular device, and in one embodiment a telescope is utilized, the telescope having an optical axis in alignment with the cornea to be measured. Mires, or illuminated targets, have the reflections thereof seen in the cornea through the telescope system. The mires generally are arranged in some manner, such as on a track whereby they can be moved toward each other or further away by rotation of a dial or the like. The image of the mires passes through condensing lenses and then through a diaphragm with four apertures. The light continues through two of the apertures without deviation. A doubling system, consisting of two adjacent prisms have one of the prisms arranged for horizontal displacement and the other for vertical displacement. Each of the prisms is placed before one of the remaining apertures resulting in four different images. The two images which are not affected by the prisms are utilized to place the instrument in proper focus much as in the manner of the coincidence range finder, that is, when the two non-affected images are coincident, the instrument is in proper focus. The focusing is accomplished by suitable adjustment of the telescope device. With two of the images coincident, upon viewing through the telescope, only three images are then seen, with a first image being in a given location, a second image in vertical alignment therewith and the third image in horizontal alignment therewith. The two doubling prisms can then be moved independently of each other to place the three images in proper alignment with each other. Since the power of each of the prisms is known, the displacement of the images can be calibrated according to the position of the prisms to determine the radius and curvature of the cornea.

The Keratometer and other similar opthalmometers utilize the same principles and have the same essential parts. Each device has an object an area bounded by the mires, which are the transluscent illuminated targets reflected by the cornea. Such instruments have a telescope for focusing the catoptric images of the mires and means for placing the images in the focal plane of the objective lens of the telescope for clearer surveyance. The examiner, or user of the instrument, must focus the hairlines within the telescope by moving the ocular lens of the telescope. At this focuses the image of the hairline in the focal plane of the objective lens, the telescope is arranged for precise observation of the images from the cornea. Such instruments also possess a doubling system which separates the images to an extent which equals the size of the images when their borders are touching. The extent of displacement is known for given positions of the prisms.

However, as a tool or instrument useful in the performance of surgery on the eye, such Keratometers and optalmometers are not suitable inasmuch as the image seen by the examiner is upside down and backwards. Additionally, the device is bulky and the monocular nature of the instrument precludes depth perception. Furthermore, measurement of radius of curvature of the cornea utilizing monocular opthalmometers or Keratometers are generally accomplished in a darkened room in order to eliminate background lighting which would hinder obtaining of the desired measurements.

An operating microscope for ophthalmic surgery is currently being manufactured and sold by Edward Weck & Company, Inc. of Long Island City, N.Y., the microscope utilizing a fibre optic light source to illuminate a circle of twelve pinpoint lights which are reflected from the cornea and superimposed within concentric rings of the eyepiece reticle during suturing of the cornea to enable the surgeon to determine when a spherical surface of the cornea has been achieved, the configuration of the reflected lights and the positioning within the appropriate concentric ring being indicative of the corneal size.

With the radius of curvature of the cornea determined prior to the operation, the surgeon attempts to reconstruct this radius after the operation. When an operation such as a cataract operation is performed, an incision is made in the Limbus or periphery of the cornea about an arc of approximately 180° of the periphery. The fluid within the anterior chamber is removed and the lens of the eye is then removed. In some instances, the lens is replaced utilizing known plastic lens implantation techniques, but in either event after the lens removal and the implantation, if performed, a saline solution is inserted into the anterior chamber and the corneal incision is then sutured. Ideally, the sutures are tensioned by the surgeon to provide the same configuration of the cornea that existed prior to the operation, that is, having the same radius of curvature. Binocular surgical microscopes are utilized in the performance of this operation to magnify the cornea to enable the delicate operation to be performed. However, even with the surgical microscope hereinabove described, the reconstruction of the corneal configuration by suitably tensioning the sutures is still very much a function of the skill of the hands and eyes of the surgeon performing the operation.

It is accordingly an object of this invention to provide a new and improved surgical microscope system.

It is another object of this invention to provide a new and improved surgical microscope system for use in an operation of the eye.

It is a further object of this invention to provide a method for utilizing the microscope as a surgical tool to reconfigure the cornea to its pre-operative condition or to reconfigure the cornea to rectify other eye disorders.

SUMMARY OF THE INVENTION

The foregoing and other objects of the invention are accomplished by providing a new and improved microscope system having means for projecting on to the cornea an image, such as a circle, with means within the microscope for optically splitting the image so-projected into a plurality of substantially identical images viewable through one or both binocular eyepieces. Means such as the zoom mechanism or rotary prisms position the images in a predetermined alignment for indicating the curvature and configuration of the cornea. The means for optically splitting the image include a plurality of prisms, lenses or mirrors insertable into the optical path within the microscope, such means being so-configured and so-positioned that a portion of the surgical field of view passes through the optical system undeviated, this portion corresponding to that portion in which the suturing is being performed. The suturing is accomplished by utilizing adjustable sutures such as slipknots which can be selectively tightened or loosened until the projected images are aligned in position and circular in configuration indicating the optimal corneal configuration. Electronic means are provided for pre-setting the microscope to a predetermined radius of curvature.

Further objects, features and advantages of the invention will become apparent upon a reading of the specification when taken in conjunction with the drawings in which like reference numerals refer to like elements in the several views.

DESCRIPTION OF THE PREFERRED EMBODIMENT

Figure 1:
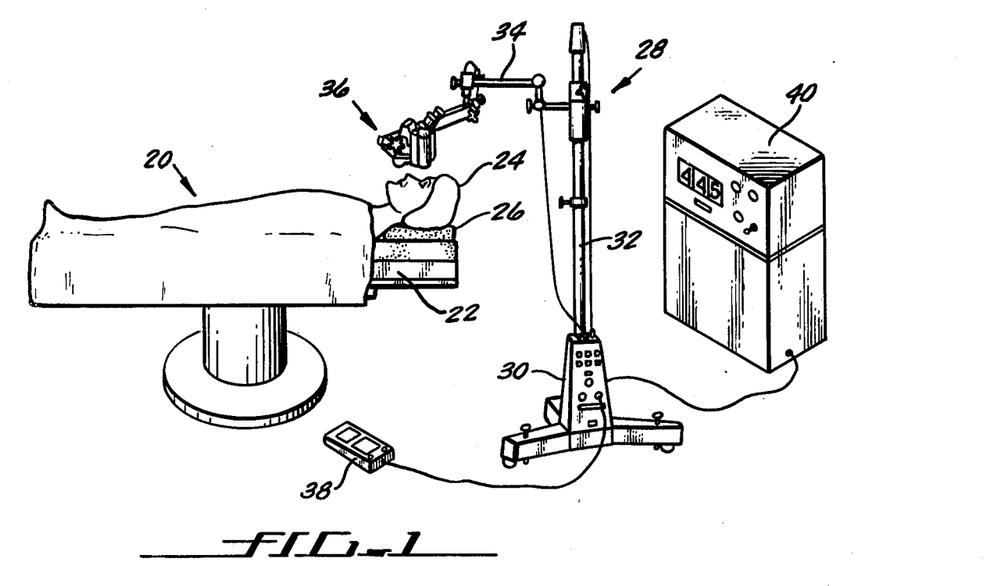
FIG. 1 is a perspective view illustrating an operating room utilizing the surgical microscope system of the invention.

Referring now to the drawings and more particularly to FIG. 1, during the performance of ophthalmic surgery on the eye, such as for cataracts or the like, the patient, generally designated 20, is placed on a suitable operating table 22 with the head 24 of the patient 20 suitably restrained such as by a head rest 26 to render the head 24 immobile. The operation is performed by the use of suitable microscope equipment generally designated 28, which includes a base 30 supporting an upright member 32, which has adjustably positioned thereon an articulated linkage 34 supporting at the free end thereof a binocular microscope assembly, generally designated 36. The binocular microscope assembly 36 is suitably positioned with respect to the eye being operated on by the physician, the objective lens thereof usually being positioned within 150 mm of the eye. The microscope assembly 36 includes a motor-operated zoom mechanism which is controlled by a suitable foot actuator or pedal 38 which is electrically coupled to the motor within the microscope assembly 36 and to a controller 40. During the performance of the operation, the surgeon performs the operation while viewing through the microscope assembly 36, and suitably actuates the foot pedal 38 in order to obtain the desired degree of magnification from the zoom mechanism within the microscope assembly 36.

Figure 2:
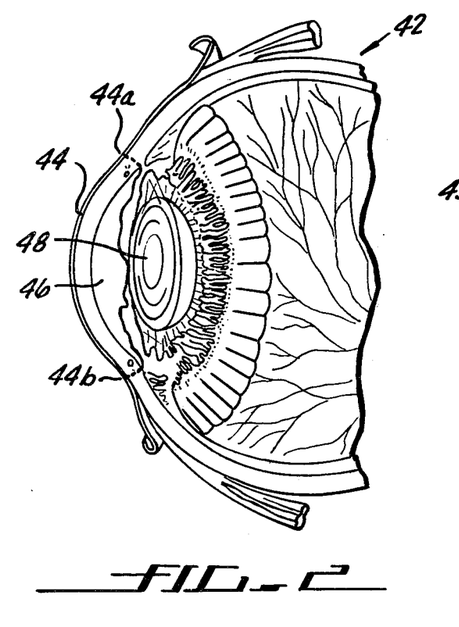
FIG. 2. is a partial cross-sectional view of the eye.

Referring now to FIG. 2, the human eye 42 is shown in cross section and includes a convex spherical surface or cornea 44, the outer limits of which are defined by the dotted lines designated 44a and 44b, the cornea 44 being generally configured as a portion of a spheroid having a given radius of curvature which is generally designated in millimeters of radius or in diopters. The cornea of the human eye generally has a radius of curvature between 6.75 millimeters and 8.0 millimeters, which is 50 to 40 diopters, respectively. Ideally, the cornea 44 which is the main focusing or refracting surface of the eye, has a spherical surface and can focus an image without distortion. Immediately behind the cornea 44 is a chamber 46 which is the anterior chamber containing fluid and is located between the cornea 44 and the lens 48. For a person suffering from cataracts, generally the condition exists as a result of the lens 48 adopting an opaque quality, and in the performance of cataract surgery the lens 48 is removed and sometimes replaced by a suitable lens implantation.

Figure 3:
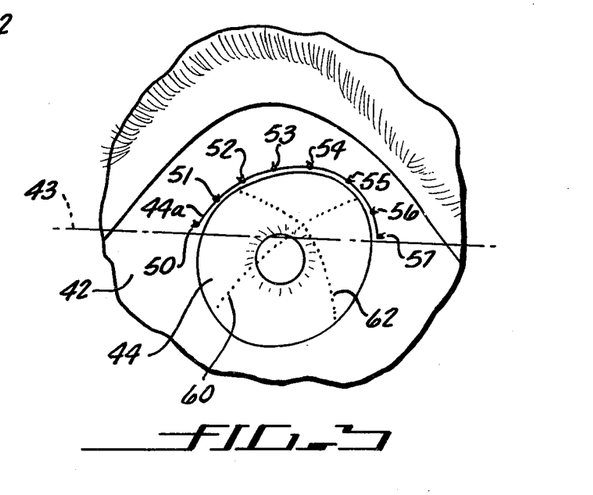
FIG. 3 is a front view of an eye depicting the incision.

With certain other diseases of the eye, the cornea is distorted from a true spherical surface to a surface which may have different radii of curvature when measured along different planes or meridians through the center of the eye, and as such, reduced visual acuity from corneal astigmatism results. In this condition the light rays passing through the cornea 44 are not brought to a single focus as a result of the distortion of the cornea. Such corneal astigmatism can also result after surgical operations if the sutures are not properly tensioned thereby distorting the corneal surface. In FIG. 3, the eye 42 is depicted from the front, and generally the surgeon is working in the upper half of the eye 42 and over the patient's head during the performance of surgery. An incision is made along the line 44a which is the periphery of the cornea through a distance of approximately 180° in the upper half of the eye 42 and in a cataract operation, the lens 48 is removed, and sometimes a plastic lens implantation is then made. A plurality of sutures 50–57 are inserted, and are equiangularly placed along the incision 44a. This incision 44a is made where the clear cornea meets the white sclera. Ideally, after the performance of cataract surgery, the contour of the cornea 44 should be spherically shaped and of the same radius of curvature that existed prior to the operation. However, without the ability to precisely adjust the tension of each of the sutures 50–57, the radius of curvature of cornea 44 that might exist, for example, along the dotted lines designated 60 and 62 can differ significantly depending on the tension of the sutures. For example, if sutures 51 and 52 are tight compared to the tension of sutures 55 and 56, the radius of curvature along line 62 would be greater than the radius of curvature along line 60 resulting in corneal astigmatism due to the non-uniform surface of the cornea 44.

As a consequence, in the performance of such surgery, a measure of the size or radius of curvature of the cornea is taken prior to the performance of the surgery and this radius of curvature is duly noted manually or electronically. The radius of curvature so-measured can be expressed either in millimeters of radius or in diopters. In accordance with the present invention, means are provided for performing this measurement in the operating room, then subsequently utilizing this measure of the radius of the curvature of the cornea to generate a pre-oriented image pattern for this measurement. Although an image pattern is visible during the suturing of the cornea, the proper image pattern exists when the corneal configuration is a spherical surface having the same radius of curvature that existed prior to the operation (or to a desired radius of curvature under certain conditions).

Figure 4:
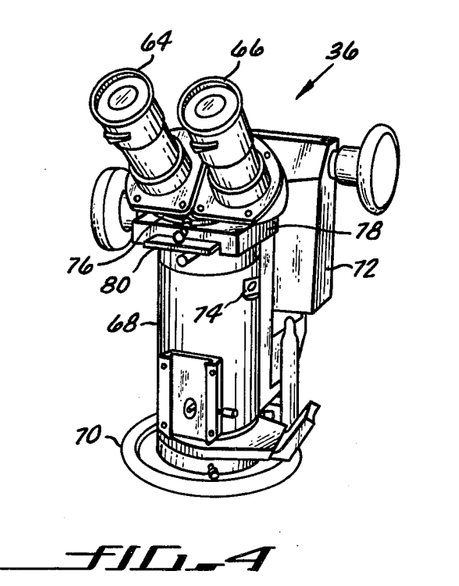
FIG. 4 is a perspective view of the binocular microscope assembly used in the apparatus of FIG. 1.

Referring now to FIG. 4, the binocular microscope assembly 36 is depicted and includes a pair of eyepieces 64 and 66, a main barrel 68, a light source 70 adjacent the lower end of the barrel 68 and a zoom control box 72, mounted rearwardly of the barrel 68. The barrel 68 contains suitable lenses for directing the light therethrough to the binocular eyepieces 64 and 66. Also located in the side of the barrel 68 is an opening or aperture 74 through which the zoom or magnification power can be determined, this magnification power being suitably inscribed on a ring within the barrel 68, the ring being coupled to the zoom mechanism to provide a visual readout indicative of the magnification. The motor for controlling the magnification or zoom is located in the motor housing 72. A suitable binocular microscope may be, for example, a Zeiss operation microscope such as the model OPMI 6 manufactured and sold by Carl Zeiss, Inc. Such an operation microscope includes a motorized zoom system with a motorized focus drive normally contained within the assembly 36 shown in FIG. 1 and suitably controlled by the foot pedal 38 to enable the surgeon's hands to remain free to perform the operation while observing through the binocular eyepieces 64 and 66. The binocular microscope assembly 36 depicted in FIG. 4 provides a stereo image to provide the surgeon with the depth of field required for performing such operations.

In the Zeiss microscope, the barrel 68 at the upper end thereof has an adapter mounting which permits removal of the eyepiece assembly designated 76 and permits the insertion therebetween of certain accessories as desired. In the embodiment shown in FIG. 4, inserted between the eyepiece assembly 76 and the barrel 68, utilizing the adaptor connection, is a prism mount 78 which includes a slidable prism tray. The light source 70 is annular in form and is secured adjacent the bottom of barrel 68 generally concentric to or coaxial with the center of barrel 68 and generally perpendicular in plane to this axis. Mechanically the Zeiss microscope is modified according to the invention by the insertion of the prism mount 78, the light source 70, and certain electrical components should be hereinafter described in connection with FIG. 10.

Figure 5:
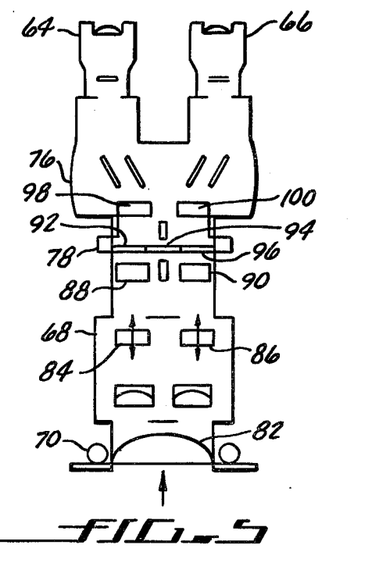
FIG. 5 is a cross-sectional diagrammatic view of the microscope of FIG. 4.

The mechanical and optical construction of the modified microscope is diagramatically depicted in FIG. 5, with the eyepieces 64 and 66 having a suitable complement of lenses and mirrors for directing light from a source such as the cornea through the bottom of barrel 68 through the main objective lens 82, which establishes a surgical field of view. Objects adjacent thereto pass through the parallel lens systems associated with each of the eyepieces 64 and 66 to provide depth of field for stereo viewing. Positioned within barrel 68 are movable lenses 84 and 86 which are suitably motor-controlled along the optical axis of each of the parallel lens arrangements to provide the zoom or magnification adjustment as required. Lenses 84 and 86 operate in conjunction with lenses 88 and 90, respectively to provide the magnification adjustments. Interposed between the lenses 88 and 90 and the main eyepiece assembly 76 is the prism mounting member 78 which is shown to contain three prisms 92, 94 and 96 which are in a generally planar array intermediate of lenses 88 and 90 and the plane of the entrance lenses 98 and 100 of the main eyepiece assembly 76. As can be seen, the prism 92 is associated solely with the light path of the eyepiece 64. Similarly the prism 96 is associated solely with the light path of the eyepiece 66 while the prism 94 therebetween directs light passing through to both the eyepiece 64 and the eyepiece 66. As will hereinafter be discussed the prisms are aligned and directed in such a manner that the images shown in FIGS. 7A–7C will result depending upon the configuration of the cornea.

Figure 6:
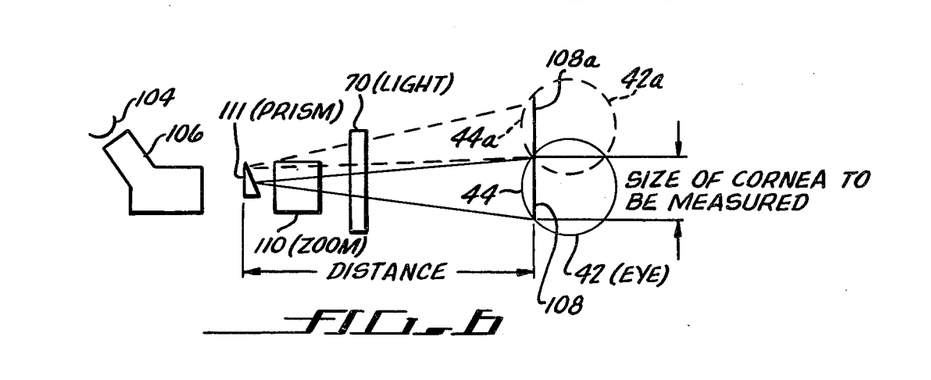
FIG. 6 is a diagrammatic view illustrating the optical arrangement in the apparatus of FIG. 1.

Referring to FIG. 6, the principal relating to the surgical microscope optical system will be discussed briefly. In principal, the device functions as a prismatic measuring system. The dimension of the cornea to be measured is a product of the prismatic deviation and the distance between the device, or microscope, and the object to be measured, that is the distance between the objective lens 82 and the cornea. The light source 70 projects a circle which is reflected off the cornea, the size and shape of which is proportional to the radius of corneal curvature. The use of a single prism would produce a doubling of the reflected circle. When the circles "touch" the corneal curvature as determined by the size of the corneal reflected image can be calculated if the power of the prism is known and the distance between the prism and the object to be measured is known. In FIG. 6, the observer's eye is diagrammatically illustrated at 104 while reference numeral 106 represents one eyepiece of a prism binocular through which the observer at 104 is viewing the eye 42 with particular attention on the cornea 44. The light source 70 is utilized to project a circle depicted by the solid line 108 on the cornea 44, this circle of light 108 being viewed through a zoom lens system 110 and through a prism 111 through the binocular 106 to be viewed by the observer 104. Due to the interception of the ring of light 108 by the prism 111 and depending upon the power of the prism 111 the original or reference image will be deviated, the observer at 104 seeing a second image displaced from the original image. This second image of the eye is shown in dotted lines and designated 42a with a corresponding displacement of the cornea, shown in dotted lines being designated 44a. Similarly, a second ring of light designated 108a appears to the observer 104. The zoom 110 is suitably adjusted to decrease or increase the diameter of the images until the circle 108 is tangential to or touching the circle 108a of the image 42a. With a known distance between the longitudinal axis of the prism 111 and the plane of the touching circles 108 and 108a; and a known prismatic deviation, the size of the corneal curvature is proportional to the magnification of the zoom mechanism 110.

Figure 7A:
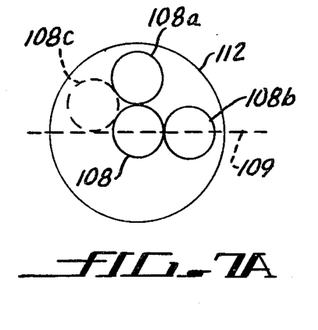
FIGS. 7A–7C are plan views depicting the image viewed through the microscope under certain conditions.

As shown in FIG. 6 with the apex of prism 111 generally vertical, the image 42a will be projected vertically upward of the actual object which is the eye 42. If a second prism is placed in the same plane as prism 111 with its apex displaced 90° to the apex of prism 111 in addition to the actual image of the eye 42 and the first projected image 42a a third image will be produced and displaced in the direction of the apex. This result is illustrated in FIG. 7A wherein the surgical field of view 112, which is generally a magnified image of the cornea, is viewed through the lens 82 in the lower part of barrel 68 of the binocular microscope assembly 36 with the original or reference ring of light image 108 abutting the previously discussed measuring image 108a and a second displaced measuring image 108b resulting from the second prism being utilized. This would be equivalent, referring to FIG. 5, of using the prisms 92 and 96 without the intervening prism 94.

Figure 7B:
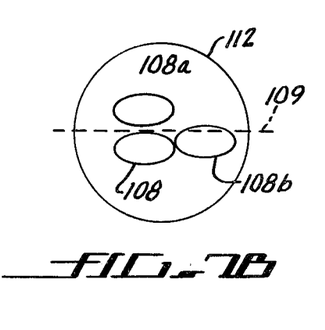
Figure 7C:
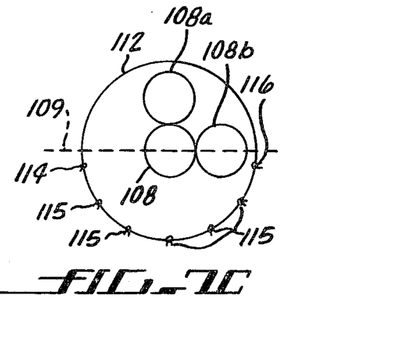

Referring again to FIG. 7A, the ring light 70 reflected off the cornea and deviated by the prisms will result in the three images 108, 108a and 108b being in the aligned relation and of the shape shown in this FIGURE when the surface of the cornea within the surgical field of view 112 is a spherical surface. The images will be tangential and circular in form. As shown in FIG. 7B, after the incision and prior to suturing the corneal surface will be irregular, thereby causing ovate images which are reflected from a corneal surface which is not spherical, the surfaces 108, 108a and 108b being of the same configuration but having an elongated form due to the irregular surface of the cornea from which the ring light 70 is reflected. FIG. 7C depicts the desired end result when sutures 114 and 116 are applied to the cornea 112 to thereby increase the radius of curvature along the line between the diametrically opposed sutures 114 and 116 thereby restoring the reference or original image and the optically formed images to a circular configuration indicative of a proper corneal configuration.

Generally, as will hereinafter be discussed, the binocular surgical microscope system according to the invention can be utilized to obtain a measurement of the radius of curvature of the cornea prior to performance of the operation, with this measure being calibrated in accordance with the magnification of the microscope system in a first embodiment, and in accordance with the relative positions of rotary prisms in a second embodiment, the calibration effectively being an indication of the rotary prism power. When used as a measuring instrument, ideally, with circular images, the surgical field of view 112 generally corresponds to an area which includes the entire cornea, but for discussion purposes FIGS. 7A-7C can be used to illustrate the periphery of the cornea. Referring to FIG. 7A, with reference to the binocular optical system diagrammatically illustrated in FIG. 5, the cornea is positioned with respect to the objective lens 82 and the annular ring light 70 so that the original reference image 108 has substantially the same center as the cornea field of view 112. The prisms 92, 94 and 96 are two diopter prisms with one measuring image 108a having its center on a diameter extending through the center of the reference image 108 with the second measuring image 108b being disposed on a second diameter generally perpendicular to the first. Although these diameters need not be perpendicular in the described embodiment a perpendicular arrangement has been selected. When viewed through the microscope the images 108, 108a and 108b may originally be in overlapping relationship, that is of larger diameter than shown, or may be of a smaller diameter, in which case they would not be touching. As a measuring instrument with the objective lens 82 a fixed distance from the corneal surface, this fixed distance generally being approximately six inches or 150 millimeters (or a pre-determined known distance), and with the ring light 70 diameter of approximately five inches, the magnification power or zoom is calibrated to provide a signal or read-out in units of diopters or millimeters of radius of curvature. The dimensions hereinabove given are not mandatory but must be known and established to provide a read-out indicative of the corneal curvature. The diagram of FIG. 7A presupposes a properly configured corneal surface. With the initial setup of the surgical microscope, for obtaining a measurement, the magnification power or zoom mechanism is operated to thereby increase or decrease the diameter of the images 108, 108a and 108b until the peripheries of the images are in touching or tangential relation as illustrated in FIG. 7A. At this point the reading is then taken to indicate the radius of curvature of the cornea.

With a known radius of curvature (or with the desired radius of curvature in other type of operations where reconfiguration of the cornea is the end objective), the surgical microscope system is then utilized during the suturing of the incision to properly tension the sutures until the images are in the alignment and of the configuration illustrated in FIG. 7A. When used for suturing purposes, the magnification power of the optical system diagrammatically illustrated in FIG. 5 is adjusted in accordance with the radius of curvature desired to pre-position the parts thereof so that the reference image reflected from the cornea, and the optically split measuring images will, only when the cornea is properly configured, result in the spatial relation of the images shown in FIG. 7A. With the optical system properly aligned, and sutures pre-positioned, but not properly tensioned, through the incision, the pre-oriented optical system will result in a field of view 112 seen through the eyepieces 64 and 66 similar to that shown in FIG. 7B. The dotted lines designated 109 generally bisects the field of view 112 horizontally into an upper half and lower half of the field of view 112. As will hereinafter be discussed, the periphery of the lower half of the field of view 112 is that area which includes the incision and in which the surgeon is operating by inserting the tensioning sutures with appropriate tools. It is therefore highly desirable that when the surgeon has the suturing tools in this area, that only one image of those tools be projected through the binocular system. Essentially then, it is preferable that this lower half of the surgical field of view remain unobstructed and that the image thereof passing through the system remain undeviated. The means of accomplishing this will be discussed hereinafter. FIG. 7C, in addition to the previously discussed sutures 114 and 116, has additional sutures 115 illustrated in the unobstructed portion of the field of view 112.

Figure 8A:
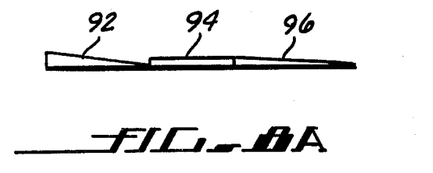
FIGS. 8A and 8B, respectively, illustrate an end view and plan view of the prism arrangement utilized in the apparatus of FIG. 1.
Figure 8B:
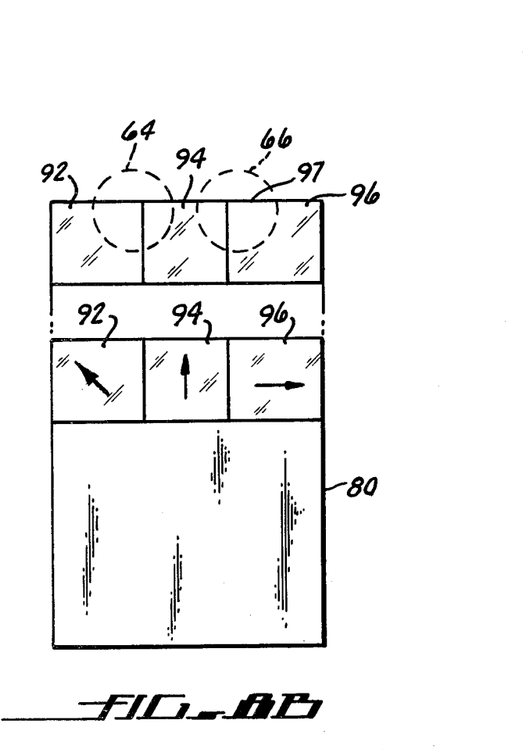

FIG. 8A illustrates an exaggerated end view showing the prisms 92, 94 and 96 with the plan view being illustrated in FIG. 8B. Referring first to FIG. 8B, the prism carrier 80 is shown diagramatically and is basically a plate-type member having secured to the ends thereof in a planar configuration the three prisms 92, 94 and 96, with the directions of the arrows thereon indicating the direction of the image displacement when viewed through the eyepieces 64 and 66. Immediately above the tray 80, the prisms 92, 94 and 96 are shown in vertically aligned relation with respect to the optical axes of the eyepieces 64 and 66, respectively, and it is to be emphasized that the prisms are so-positioned with respect to the optical axes to leave a portion or approximately half the surgical field of view unobstructed by the prism array to permit the uninterrupted and undeviated passage of the image of the upper half of the cornea, the upper half of the cornea being that area in which the operation is to be performed and the sutures 50-57 are to be inserted in the cornea 44 (see FIG. 3). The reflected or deviated images of the three prisms 92, 94 and 96 are in the directions of the arrows indicated thereon, each of the arrows pointing toward the apex of the respective prism. Referring again to FIG. 7A, the image which will appear on cornea 112 as a result of a three prism array depicted in FIGS. 8A and 8B are illustrated. The circle 108 is the original or reference ring light image while the circle 108a results from the prism 94, the circle 108b results from the prism 96 and the circle depicted in dotted lines and designated 108c will result from the prism 92. The prisms 92, 94 and 96 are each two diopter prisms.

In any event, the planar array of prisms have the apexes thereof angularly displaced with respect to each other, with the prisms arranged to form a leading edge 97 which is positioned at the approximate mid-point with respect to the optical paths of binocular eyepieces 64 and 66 to optically split the image of the reflected light ring appearing on the cornea. Since the prisms intercept only half the projected image, the other half of the image will appear uninterrupted in the binocular eyepieces thus creating a clear field of approximately one-half the cornea, this clear field corresponding to that in which the surgeon operates. For example, referring to FIG. 3, a horizontal broken line designated 43 is at the approximate midpoint of the cornea 44 (also illustrated as line 109 in FIGS. 7A-7C). The portion above the line which includes the incision 44a is that area in which the surgeon operates utilizing tools to create the incision 44a and utilizing other tools to perform the suturing. This area remains unobstructed in the field of view of the surgeon and although three or four images are projected and observed as seen in FIG. 7A, the original image 108 will be the only image in which the surgeon's tools appear. Complete optically split images 108a, 108b and 108c are formed as a result of the optical arrangement diagrammatically illustrated in FIG. 5 in which the planar array of prisms 92, 94 and 96 are displaced from the plane of the fixed lenses 88 and 90 associated with the zoom and magnification mechanism, as well as being spaced from a plane of the fixed lenses 98 and 100 contained within the binocular eyepiece assembly 76.

Although, as shown in FIG. 7A in solid lines, two prisms creating the original image 108 plus two optically split images 108a and 108b can accomplish the intended result of providing a quantitative surface measurement, the use of three prisms to generate the additional image 108c shown in dotted lines is more accurate for the following reason. As can be seen in FIG. 7B, when the corneal surface is distorted ovate images are projected and with only three images appearing, if the corneal surface is slightly ovate, the three images can appear to be tangential which would indicate a proper corneal surface of a spherical configuration. However, since the ovate images are elliptical in form, two mutually perpendicular lines are necessary to define an ellipse, that is 4 points, and by projecting the fourth image utilizing the three prisms, if the images were only slightly elliptical, this would immediately become apparent.

Figure 9A:
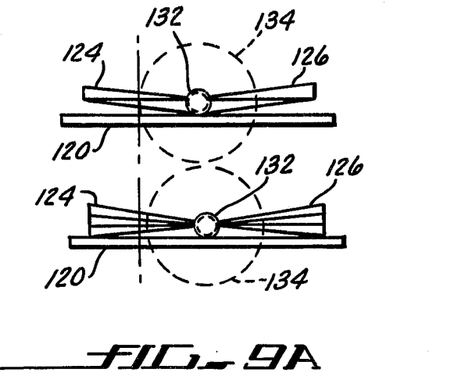
FIGS. 9A and 9B are end views and a plan view, respectively, of an alternate embodiment of prism arrangements for use in the apparatus of FIG. 1.
Figure 9B:
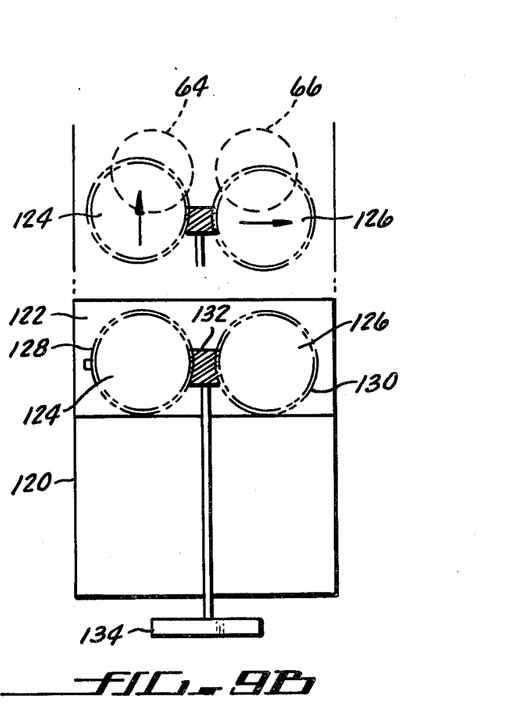

Referring now to FIGS. 9A and 9B, a second embodiment is illustrated utilizing rotary prisms in a non-zoom microscope system. As shown in FIG. 9B a prism tray 120 is provided with the upper edge 122 thereof being generally optically clear and having rotatably mounted therein first and second rotary prisms 124 and 126 which are provided about the periphery thereof with ring gear portions 128 and 130, respectively. The ring gear portions 128 and 130 coact with a worm gear 132 which is thumbwheel 134 operated to simultaneously rotate the rotary prisms 124 and 126 in opposite directions. Shown immediately above the prism tray 120 in FIG. 9B the upper portion thereof is shown in alignment with the optical paths of binocular eyepieces 64 and 66, with each of the rotary prisms 124 and 126 intercepting approximately one-half the light passing through the eyepieces. On each of the prisms 124 and 126 there is an arrow thereon indicating the angular displacement of the optically split images created thereby to effectively result in the projected images shown in solid lines in FIG. 7A. The arrows on the prisms 124 and 126 also illustrate the effective apex alignment of each of the rotary prisms, and if, for example, rotary lens 126 were rotated in a counterclockwise direction, rotary lens 124 would be rotated in a clockwise direction, thus reorienting the effective apex alignments relative to each other and consequently displacing the images viewed through the eyepieces 64 and 66. When a fixed magnification power on the microscope the thumbwheel 134 will be rotated until the images projected are tangentially aligned. FIG. 9A illustrates the planar arrangement of the rotary prisms 124 and 126 with respect to each other at mutually perpendicular angular displacements relative to each other. Upon rotation of the thumbwheel 134, the amount of deviation of light through each prism is varied, thereby effectively varying the prism diopter rating of the prisms within a given range.

In the second embodiment of the prism array illustrated in FIGS. 9A and 9B, the image size viewed through the microscope will remain constant in diameter with a non-zoom microscope system, and rotation of the thumbwheel 134 will affect the alignment of each of the optically produced images formed by passage through the rotary lenses 124 and 126 with respect to the original or referenced image 108 (FIG. 7A). With the prism diopter range of the rotary prisms known, and again with the objective lens a predetermined distance from the cornea, and also with a given diameter of image creating source, such as ring light 70, the amount of realignment of the optically produced images 108a and 108b will be indicative of the corneal radius of curvature. As a consequence, the thumbwheel 134 can be suitably coupled to an electrical sensing device such as a rheostat to provide an electrical signal indicative of the amount of rotation required to place the images in alignment as depicted in FIG. 7A. It is also to be understood however that while the embodiments of FIGS.

8A and 8B depict prisms, lenses and mirrors can likewise be utilized to create or optically produce the measuring images viewed through the binocular eyepieces. Similarly, although the image shown and herein described is a circular image, other images can be utilized and the alignment thereof need not be in a tangential relation but must be in a pre-determined relation. Preferably, the other images could be suitably employed with the radially symmetrical images.

Figure 10:
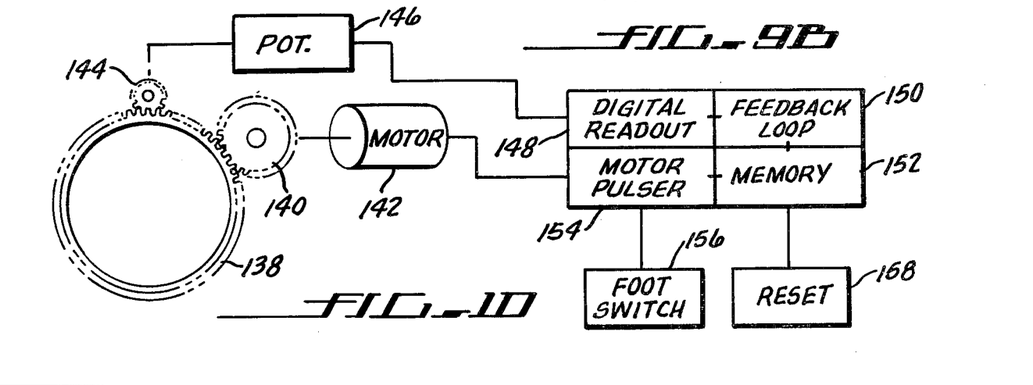
FIG. 10 is a diagrammatic view of the electrical/mechanical interfacing components of the system of FIG. 1.

In the surgical microscope system using the first embodiment of splitting or producing the images magnifications of 7 to 20 power are generally obtainable with the magnification or zoom being motor-operated. Referring to FIG. 10, a ring gear 138 is shown, the ring gear 138 fitting within the barrel 68 (see FIGS. 4 and 5) of the microscope, with the periphery thereof bearing numerals viewable through the aperture 74. The ring gear 138 is adapted to move the lenses 84 and 86 with respect to the fixed lenses 88 and 90, respectively, to provide the magnification or zoom for the microscope.

As shown in FIG. 10, the ring gear 138 is in meshing engagement with a gear member 140 which is operated by means of a motor 142 which is reversible and may be, for example, a direct current motor. Normal operation of the motor 142 in the surgical microscope shown in FIG. 1 is by means of the foot pedal 38. In accordance with the present invention, additional control means are provided, these control means being illustrated in FIG. 10 and including a second gear member 144 coupled to the ring gear 138 to be driven thereby. The driven gear 144 is coupled to a suitable position sensing means such as a potentiometer 146 which is preferably a precision multiturn potentiometer having the slide thereof coupled to be driven in response to rotation of gear member 144, thus providing an electrical signal indicative of the magnification power of the zoom lens. With the images touching as shown in FIG. 7A, this magnification power will correspond to an indication of the radius of curvature of the cornea prior to the performance of the surgery. The electrical signal so-received as a result of the position or resistance of potentiometer 146 is coupled to a digital readout subassembly 148 to provide a direct readout either in diopters or radius of curvature on a digital display. The signal present in the digital readout subassembly 148 provides an electrical signal for a feedback loop 150, this digital readout also being stored in a memory 152. Once the original corneal reading is obtained, the prism tray 80 can be removed to permit the surgeon to create the incision and perform the lens implantation while utilizing the entire surgical field of view. During the operation, however, the distance between the eye and the binocular microscope assembly 36 remains unchanged although the magnifying power may be altered during the course of the operation to permit additional viewing of the lens 48, for example, during the lens implantation in cataract surgery. When the surgeon has completed the lens implantation and is preparing to suture the incision, the prism tray 80 is replaced to its approximate mid-point and the digital readout stored in the memory 152 actuates a motor pulser 154 to reposition the ring gear 138 to that magnifying power indicated by the reading within the memory 152. This position would indicate the original corneal configuration. The foot switch 156 can be a multiposition foot switch with an override position or a position which merely instructs the motor pulser to go to that magnifying power indicated by the memory 152.

A reset circuit 158 is also provided to reset the memory 152.

Figure 11:
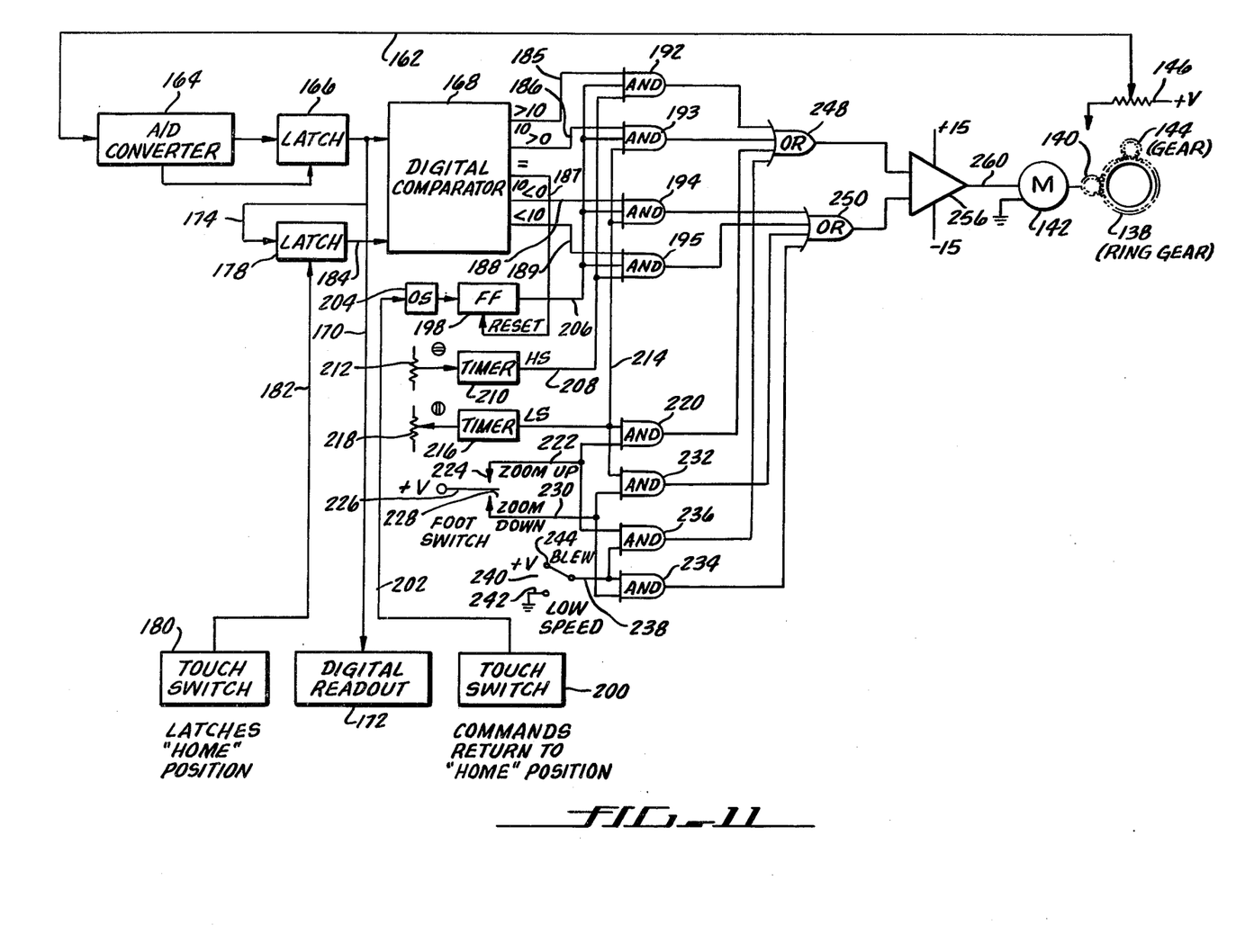
FIG. 11 is an electrical block diagram of the electronic circuitry utilized in the apparatus of FIG. 1.

The diagrammatic electrical system shown in FIG. 10 is more fully illustrated in FIG. 11 and illustrates the ring gear 138 coacting and driven by the gear 140 connected to motor 142. The motor 142 can be, for example, a direct current gear motor to provide an appropriate gear reduction between the speed of the motor 142 and the speed of the drive gear 144. As previously discussed, the position of ring gear 138 is indicative of the magnification power of the microscope assembly 36 and this position is electrically indicated by means of the gear 144 suitably positioning the slide tap 160 on the potentiometer 146 which has the ends thereof coupled between a positive source of voltage (+V) and ground. As a result, the position of the slider 160 with respect to potentiometer 146 provides an analog signal which is transmitted over lead 162 to an analog to digital converter 164. The digital output is then fed into a latch 166, the output of which is provided to a first input of a digital comparator 168 and also over lead 170 to a digital readout 172. The output of latch 166 is also fed over lead 174 to a second memory or latch 178. The latch 178 is set by means of a touch switch 180 providing an input to latch 178 over lead 182. The latch 178 provides the second input over lead 184 to the digital comparator 168.

Depending on the value of the digital outputs of latches 166 and 178, pulses are transmitted over one of five output leads 185–189 of digital comparator 168, each of the output leads 185, 186, 188 and 189 being connected to provide a first input to AND gates 192–195, respectively. Output lead 187 of digital comparator 186 has a pulse output when the two input signals from latches 166 and 178 are identical, thereby providing a "reset" pulse to flip-flop 198. The flip-flop 198 is a bi-stable multi-vibrator which is "set" by means of actuation of a second touch switch 200 which provides a signal over lead 202 to a one-shot multi-vibrator 204, the output of which sets the flip-flop. The output of flip-flop 198 is transferred over lead 206 to provide a second input to each of the AND gates 192 and 195, respectively. The third input to each of the AND gates 192 and 195 is provided over lead 208 from a high speed timer 210, the timer 210 being essentially a pulse generator which has the pulse width for pulse frequency suitably pre-set to a high speed and adjustable within a limited range by means of a rheostat 212.

The third inputs of AND gates 193 and 194 are provided over lead 214 from a second or low speed timer 216, which similarly is a pulse generator providing low speed pulses of a predetermined frequency or pulse width similarly controlled by a rheostat 218. The output of timer 216 is also fed to a two input AND gate 220, which has the other input thereof coupled over head 222 to a first contract 224 which is the "zoom up" contact of the foot switch schematically illustrated. The movable contact 226 of the foot switch is coupled to a positive voltage source +V and can be actuated between contact 224 or contact 228 which is the "zoom down" contact. Contact 228 is coupled over lead 230 to provide a first input to AND gate 232 and a first input to AND gate 234. Contact 224 is coupled over lead 222 to provide a first input to AND gate 236. The second input to AND gates 234 and 236 are provided over lead 238 from a two-position manually controlled switch 240 operable between a low speed contact 242 connected to ground and a "slew" contact 244 coupled to a positive source of voltage.

The outputs of AND gates 192, 193, 220 and 236 provide inputs to a four input OR gate 248. The outputs of AND gates 194, 195, 232 and 234 provide inputs to a four input OR gate 250. The outputs of OR gates 248 and 250 are coupled to the two inputs of an operational amplifier 256 which is biased between positive and negative voltage sources to provide polarity reversing over the output lead 260 thereof to the motor 142 to suitably control the speed and direction of rotation of motor 142.

In operation, the controller electronic system shown in FIG. 11 works as follows. When the surgeon is operating the microscope system to set up the initial image position shown in FIG. 7A, the operation of the system is effected by means of the foot switch which is actuated between the "zoom up" position or contact 224 and the "zoom down" position or contact 228. The high speed timer 210 and the low speed timer 216 are operative upon system energization. If the movable contact 226 of the foot switch is actuated to the "zoom up" position, AND gate 220 is enabled by means of the input signal over lead 222 and the output of the low speed timer 216, the output of AND gate 220 being fed through OR gate 228 to the positive input of operational amplifier 256. Operational amplifier 256 is used as a switch and amplifies the input pulse of approximately 5 volts to an output of approximately 12 volts, this output being transmitted over lead 260 to energize motor 142 in a direction to increase the magnification power. As the ring gear 138 rotates to the desired position, the potientiometer gear 144 correspondingly rotates to reposition slide 160 of potientiometer 166, thereby providing an analog signal indicative of the position of ring gear 138. This analog signal is fed over lead 162 to the analog digital converter 164 where the first and second outputs thereof are provided to latch 166 to provide a digital signal corresponding to the analog voltage appearing at slider 160 of the potientiometer 146. The digital content of latch 166 is continually updated in accordance with the analog position. The output of latch 166 is suitably displayed by means of the lead 170 coupling the output to the digital readout 172. The digital display then provides a measure of radius of curvature either in diopters or millimeters of radius depending upon the initial system setup.

When the images seen through the binocular lenses correspond to that shown in FIG. 7A, the surgeon then actuates touch switch 180 to transmit a pulse over lead 182 to latch 178 which latches in the digital content of latch 166 by virtue of the interconnection of lead 174. The latch 178 is essentially a memory which retains the original digital measurement. This measurement is then stored for the duration of the surgical operation. After the conclusion of the lens implantation in a cataract operation, for example, the surgeon then depresses momentarily the second touch switch 200 which commands the system of FIG. 11 to return to the "home" position, that is, the rotational position of ring gear 138 in accordance with the instructions stored in latch 178.

To return the magnification power to the prescribed position, the digital comparator 168 compares the real time digital content of latch 166 with the target or indicated content of latch 178 and provides one of five outputs depending upon the differential in value between the two inputs. If the differential value is large, the output of digital comparator directs that the motor 142 be fed pulses from the high speed timer 210 to thereby provide a high speed of rotation of motor 142. As the value of the differential between the two imput values decreases, the output of the digital comparator occurs over another lead which when directs that the motor 142 be fed pulses from the low speed timer 216 to assist in precise positioning of the ring gear 138 with respect to its desired position.

Briefly, output lead 185 of digital comparator 168 enables high speed pulses to increase the magnification while an output appearing on lead 186 enables low speed pulses to increase the magnification. Similarly, pulses appearing on output leads 188 and 189, respectively, direct low speed and high speed pulses, respectively, to be applied to motor 142. The digital comparator 168 is set up on a "decade" basis and when the differential between the input of latch 166 and 178 are greater than one decade, and obviously depending upon the polarity, the output pulse appears either on lead 185 or lead 189. If the differential between the inputs is between zero and one decade, the output of digital comparator 168, again depending upon the output of latch 166 being above or below the contents of latch 178, the output pulse from digital comparator 168 will appear on lead 186 or lead 188. When a null or balance position is reached between the two inputs, the output of digital comparator 168 will appear on lead 187.

When touch switch 200 is actuated, lead 202 is energized to actuate the one-shot multi-vibrator 204 to set the flip-flop 198 which remains set to enable a first input of all AND gates 192–195, each of these AND gates having as a second input one of the input leads 185, 186, 188 and 189 from the digital comparator 168. At this time, with the foot switch inactive with the movable contact 226 intermediate stationary contacts 224 and 228, the AND gates 220, 232, 236 and 234 are disabled rendering motor control fully automatic. With any of the AND gates 192–195 enabled, depending upon the difference between the inputs to digital comparator 168, either OR gate 248 or 250 will be enabled to provide a signal to the reversing or non-reversing inputs of the operational amplifier 256 to suitably control the direction and speed of rotation of motor 142 to position ring gear 138 at the position indicated by the digital content of latch 178. When the "null" or balance position is reached, the digital comparator 168 will provide a pulse output over lead 187 to reset the flip-flop 198 thereby disabling the AND gates 192–195, respectively. If desired, the output appearing on lead 187 can also be utilized to energize an indicating lamp indicative of the "home" position being achieved, that is, that a null balance position exists. At this point, the surgeon can then perform the suturing required to close the incision.

By utilization of the system described, if the original digital readout during the measuring of the patient's eye, prior to the operation, was 44.5 diopters, this number will be digitally stored in latch 178 and after completion of the cataract extraction the desired magnification will be restored to a reading of 44.5 diopters. The surgeon viewing the images through the binocular eyepieces 64 and 66, prior to suturing will see images similar to FIG. 7B with a fourth image if three prisms are used. These images as previously discussed will be somewhat elliptical or ovate in form and will not be tangential.

Figure 12A:
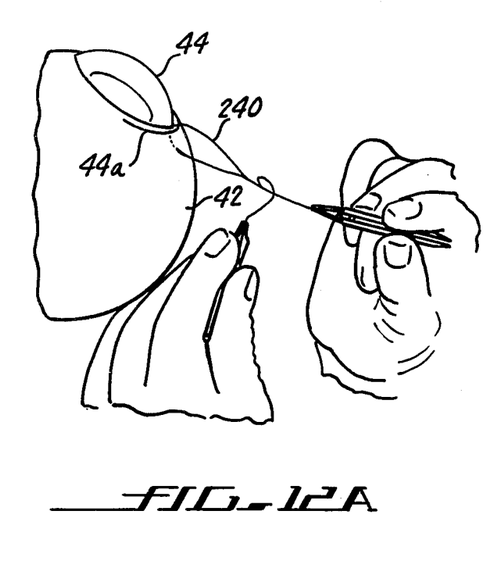
FIGS. 12A–12C are perspective views of a simulated eye depicting the suturing sequence.
Figure 12B:
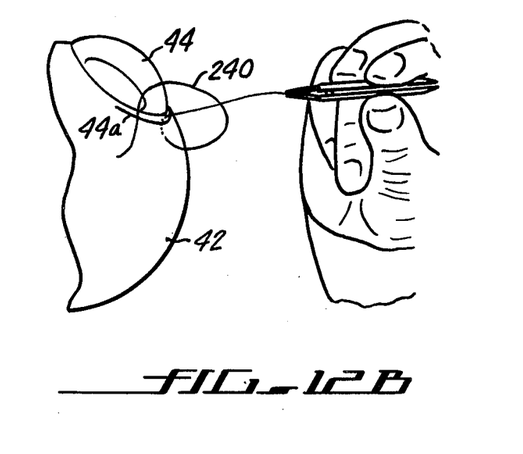
Figure 12C:
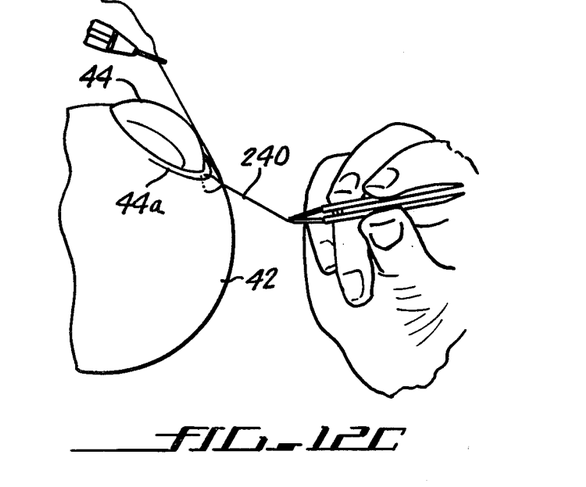

With the portion of the cornea in which the suturing is to be effected passing through the binocular microscope unobstructed, the surgeon is in a position to insert the sutures in the sequence shown in FIGS. 12A–12C.

In FIG. 12A, the suturing material 240 is inserted through the sclera and through the cornea 44 of the eye 42 on either side of the incision 44a. As shown in FIG. 12B the suturing material 240 is then formed into a slip knot to provide an adjustable suture whereby the slip knot can be adjusted to varying degrees of tension as required to construct the generally spherical surface of the cornea 44 after the suturing is completed. The slip knot is then adjusted to a nominal tension situation until the eight stitches 50–57 shown in FIG. 3 are equiangularly positioned through an arc of approximately 180° to close the incision 44a. The sutures 50–57 are then selectively tightened or loosened so long as the image shown in FIG. 7B is projected. Although the elliptical images 108, 108a and 108b are shown as extending in a generally horizontal direction, it is to be understood, that depending upon the tightness or looseness of the various stitches the image of the reflected light as seen through the binocular eyepiece can be displaced at other angles generally with the major axis of each of the images extending in the same direction. In any event, the sutures 50–57 have the tension thereof suitably adjusted until the image shown in FIG. 7C is achieved. Once all the slip knot sutures have been adjusted, as shown in FIG. 13C a second knot is then placed overlying the original slip knot to form a square knot and thus secure the so-adjusted sutures.

By utilization of the apparatus and method hereinabove described the radius of curvature of the cornea can be restored to that radius existing prior to the operation. In normal cataract surgery without the utilization of the surgical microscope system hereinabove described, the radius of curvature after cataract surgery could normally be expected to be within a range of 1 to 8 diopters of the original corneal radius curvature depending upon the skill of the surgeon. By the utilization of this sytem, precision is obtainable after suturing within 0 to 1 diopters of the original radius of cuvature of the cornea.

Essentially, the operation is performed as follows. Prior to the operation, utilizing the binocular microscope assembly 36 as shown in FIG. 4, with the prism array of FIG. 8, the light source 70 is energized thereby projecting a circle of light onto the cornea of the patient. With the prism tray 80 positioned to intercept approximately half the image, four circles of light appear through the eyepieces 64 and 66. The zoom motor of the microscope is then energized until the original image 108 and measuring images 108a–c are in the aligned relationship as shown in FIG. 7A and a digital readout measured in diopters or millimeters of radius of curvature is obtained through the electronic system of FIG. 11. This digital readout is then appropriately recorded in memory to provide an indication of the actual preoperative corneal radius of curvature. The incision is then made, and in the case of a cataract operation, a lens implantation is made through the incision which, in accordance with normal surgical procedures, extends through an arc of approximately 180° of the periphery of the cornea. After the lens implantation, equi-angularly displaced sutures preferably totalling eight sutures, are used to close the incision. Each of the sutures has a first slip knot formed therein to render each of the eight sutures adjustable in tension to thereby permit adjustment of the corneal curvature in accordance with the images observable through the binocular eyepieces 64 and 66. With the area in which the surgeon is working having the image thereof unobstructed, the surgeon will be viewing only one image which will show the tools with which he is working. The optically split images will appear as measuring images through the microscope without the tools. As the tools approach the midline (shown as line 109 in FIG. 7A) the tools will appear with the measuring images, but are of diminished intensity, and hence, not objectionable.

Generally, the images prior to adjustment will be elliptical or ovate in form and have angular orientations with respect to the cornea depending on the relative tension of each of the sutures with respect to the others. The sutures can then be alternately loosened or tightened until all images are circular in form and tangential at the prescribed initial radius of curvature reading previously obtained, thereby indicating that the corneal surface after suturing corresponds to the corneal surface prior to the operation. Each of the sutures is then tied with a second square knot to secure it in place.

While there has been shown and described a preferred embodiment, it is to be understood that various other adaptations and modifications may be made within the spirit and scope of the invention.

What is claimed is:

1. A surgical microscope for use during suturing of an incision in the cornea to reconstruct the cornea of an eye in accordance with a predetermined radius of curvature, the combination comprising:

a binocular microscope having an entrance lens adapted to be positioned a fixed distance from the eye to provide a surgical field of view through the eyepieces;

means adjacent said entrance lens for projecting a reference image on said cornea;

means positioned at least partially within said microscope for optically forming at least one other substantially identical image viewable through said microscope with said reference image, said means being so-positioned to permit a portion of the reference image to pass through said microscope undeviated with the undeviated portion of said reference image being in the portion of the cornea where the incision has beem made; and means for adjusting at least one of the magnification power of said microscope and the optical alignment of said optical forming means for varying said reference image and said at least one other substantially identical image into a predetermined image pattern, said predetermined image pattern being viewable through said microscope only when the sutures of the incision are properly tensioned to provide the predetermined radius of curvature.

2. The combination according to claim 1 wherein said microscope is a variable magnification microscope and said means for adjusting are means for adjusting the magnification power to a predetermined power calibrated to the predetermined radius of curvature whereby said reference image and said at least one other substantially identical image are varied in size to provide said predetermined alignment.

3. The combination according to claim 2 wherein said means for optically forming at least one other image includes prism means.

4. The combination according to claim 3 wherein said prism means positioned within said microscope include a prism array of at least two prisms for optically forming at least two other substantially identical images, each of said prisms being oriented with respect to each other and with respect to the optical axis of the microscope to deviate the reference image reflected from the corneal surface at predetermined angles to pre-orient an image pattern.

5. The combination according to claim 3 wherein said prism means includes a prism array of at least three prisms for optically forming at least three other substantially identical images, each of said prisms being oriented with respect to each other and with respect to the optical axis of the microscope to deviate the reference image reflected from the corneal surface at predetermined angles to pre-orient an image pattern.

6. The combination according to claim 5 wherein each of said prisms has the same diopter power rating.

7. The combination according to claim 6 wherein said prisms are positioned in a generally planar array with the apexes thereof angularly displaced with respect to each other, the prisms being arranged to form a leading edge which is positioned at the approximate mid-point of the optical paths of the binocular eyepieces.

8. The combination according to claim 7 wherein the means for projecting the reference image is a circular light source.

9. The combination according to claim 8 wherein said circular light source is positioned adjacent said entrance lens generally perpendicular to the optical axis of the microscope and concentric with the surgical field of view.

10. The combination according to claim 1 wherein said microscope has a fixed magnification power and said means for optically forming said at least one other image include rotary prism means for varying the prism power and the position of said at least one other image with respect to said reference image.

11. The combination according to claim 10 wherein said rotary prism means includes first and second rotary prisms positioned within said microscope to at least partially intercept the optical paths of each of the binocular eyepieces to form two other substantially identical images.

12. The combination according to claim 11 wherein said first and second rotary prisms are mounted on a tray in a generally planar arrangement, the tray being movable in a direction perpendicular to the optical axis of said microscope.

13. The combination according to claim 7 wherein said prisms are mounted on a tray, the tray being movable in a direction perpendicular to the optical axis of said microscope.

14. In a microscope system for use during ophthalmic surgery on the cornea, the combination comprising:
 a binocular microscope having an entrance lens adapted to be positioned a fixed distance from the eye to provide a surgical field of view through the eyepieces;
 means adjacent said entrance lens for projecting a reference image on said cornea;
 means for optically splitting said reference image to produce a plurality of substantially identical images;
 means for adjusting the optical system for adjusting the images so formed into a predetermined image pattern;
 means responsive to said adjusting means for providing an output indicative of the radius of curvature of the cornea; and
 storage means for storing the output.

15. The combination according to claim 14 further including control means coupled to said storage means and said adjusting means for adjusting the optical system in response to said output whereby to enable the surgeon to restore the adjustment of the optical system prior to suturing the incision to pre-orient the image pattern indicative of the pre-operative radius of curvature.

16. The combination according to claim 15 wherein said means for optically splitting the reference image includes prism means positioned at least partially within said microscope to permit a portion of the reference image to pass through said microscope undeviated whereby to allow the surgeon an unobstructed portion of the surgical field of view in the region of suturing.

17. The combination according to claim 16 wherein said prism means includes three prisms of the same prism power and of generally the same overall configuration positioned in abutting relation in a planar array with the apexes of each of the prisms being oriented with respect to each other and with respect to the optical axis of the microscope to deviate the reflected reference image at predetermined angles to pre-orient an image pattern.

18. The combination according to claim 17 wherein said binocular microscope is a variable magnification microscope and said means for adjusting the optical system are means for adjusting the magnification power to a predetermined power calibrated to the predetermined radius of curvature whereby the images are varied in size to provide the predetermined image pattern.

19. The combination according to claim 18 wherein said prisms are mounted in a rectangular configuration having a leading edge which is positionable within the optical path of the binocular eyepieces.

20. The combination according to claim 19 wherein said system includes means for digitally displaying the radius of curvature.

21. The combination according to claim 20 wherein said means for adjusting the magnification power include motor-operated gear means.

22. The combination according to claim 21 wherein said motor-operated gear means includes other means coupled to said gear means for providing an analog signal proportional to the magnification power.

23. The combination according to claim 16 wherein said prism means includes rotary prisms positioned in a common plane with each of the prisms being in the optical path of one of the eyepieces, and said means for adjusting the optical system are means for rotating said rotary prisms whereby the image positions are varied to provide the predetermined image pattern.

24. The combination according to claim 23 wherein said rotary prisms are mounted on a tray slidable in a direction generally perpendicular to the optical axis of the microscope.

25. The combination according to claim 24 wherein said means for projecting a reference image includes a circular light source.

26. The combination according to claim 25 wherein said circular light source is in a plane perpendicular to the optical axis of the microscope and generally concentric therewith.

27. The combination according to claim 26 wherein rotation of said rotary prisms varies the diopter rating and consequently the angle of deviation.

28. In a method for use during suturing of an incision adjacent to the cornea to reconstruct the cornea of an eye in accordance with a predetermined radius of curvature, the combination comprising:

projecting a reference image onto the surface of the cornea;

placing a binocular microscope with the field of view thereof receiving the reflected light image for viewing through said microscope;

optically forming at least one other substantially identical image for viewing through said microscope; and optically varying said reference image and said at least one other image to establish a predetermined image pattern viewable through said microscope only when the sutures of the incision are properly tensioned to provide a predetermined radius of curvature.

29. The combination according to claim 28 wherein the step of optically varying the images comprises adjusting the magnification power of the microscope to a power correlated to the predetermined radius of curvature.

30. The combination according to claim 27 wherein the step of optically varying the images comprises adjusting means within the microscope for optically forming said at least one other image to vary the position of said at least one other image with respect to said reference image.

31. In a method for use during ophthalmic surgery utilizing a given binocular microscope system having a microscope providing a surgical field of view of the eye, the combination comprising:

projecting a reference image onto the surface of the cornea prior to the making of an incision;

optically forming at least one other substantially identical image for viewing through said microscope;

optically varying said reference image and said at least one other image into a predetermined image pattern;

providing an electrical signal indicative of the optical varying required to establish said predetermined image pattern; and setting the microscope system in accordance with said electrical signal after the incision has been made and prior to suturing, said predetermined image pattern being viewable through said microscope only when the sutures are properly tensioned whereby to reconstruct the radius of curvature of the cornea to that radius existing prior to the operation.

* * * * *